US012778856B2

(12) United States Patent
Sato et al.

(10) Patent No.: US 12,778,856 B2
(45) Date of Patent: Nov. 3, 2026

(54) DENTAL ADHESIVE COMPOSITION

(71) Applicant: GC Corporation, Shizuoka (JP)

(72) Inventors: Yuna Sato, Tokyo (JP); Sayaka Higashi, Tokyo (JP); Hiroto Minamisawa, Tokyo (JP)

(73) Assignee: GC Corporation, Shizuoka (JP)

( * ) Notice: Subject to any disclaimer, the term of this patent is extended or adjusted under 35 U.S.C. 154(b) by 421 days.

(21) Appl. No.: 18/696,575

(22) PCT Filed: Sep. 26, 2022

(86) PCT No.: PCT/JP2022/035780
§ 371 (c)(1),
(2) Date: Mar. 28, 2024

(87) PCT Pub. No.: WO2023/054284
PCT Pub. Date: Apr. 6, 2023

(65) Prior Publication Data

US 2025/0041163 A1 Feb. 6, 2025

(30) Foreign Application Priority Data

Sep. 30, 2021 (JP) ................................. 2021-162363
Sep. 6, 2022 (JP) ................................. 2022-141589

(51) Int. Cl.
*A61K 6/30* (2020.01)
*A61K 6/62* (2020.01)
*C08L 51/08* (2006.01)

(52) U.S. Cl.
CPC .................. *A61K 6/30* (2020.01); *A61K 6/62* (2020.01); *C08L 51/085* (2013.01)

(58) Field of Classification Search
CPC combination set(s) only.
See application file for complete search history.

(56) References Cited

U.S. PATENT DOCUMENTS

2012/0123045 A1 5/2012 Mitomi et al.
2012/0245272 A1* 9/2012 Dent ...................... C08G 77/50 524/502
2014/0138864 A1* 5/2014 Plaumann .............. A61K 6/887 523/116
2021/0145701 A1* 5/2021 Nojiri ...................... A61K 6/30

FOREIGN PATENT DOCUMENTS

| | | |
|---|---|---|
| EP | 3409703 | 12/2018 |
| EP | 3540022 | 9/2019 |
| EP | 3567084 | 11/2019 |
| JP | 2002-053418 | 2/2002 |
| JP | 2014-208826 | 11/2014 |
| JP | 2017-014385 | 1/2017 |
| JP | 2019-151595 | 9/2019 |
| JP | 2020-002076 | 1/2020 |
| WO | 2011/013789 | 2/2011 |
| WO | 2019/172132 | 9/2019 |
| WO | 2019/203356 | 10/2019 |
| WO | 2020/066420 | 4/2020 |
| WO | 2020/136614 | 7/2020 |

OTHER PUBLICATIONS

International Search Report mailed on Dec. 6, 2022 with respect to PCT/JP2022/035780.
Ge, Xueping et al., Synthesis and evaluation of novel siloxane-methacrylate monomers used as dentin adhesives, Dental Materials, 2014, vol. 30, pp. 1073-1087 Abstract , Materials and methods , Results.

* cited by examiner

*Primary Examiner* — Peter A Salamon
(74) *Attorney, Agent, or Firm* — IPUSA, PLLC

(57) ABSTRACT

A dental adhesive composition including: a (meth)acrylate having an acid group; and a linear siloxane represented by a general formula (1).

[Chem. 1]

(1)

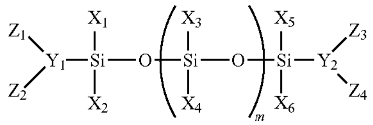

In the general formula (1), $X_1$ to $X_6$ are independently an alkyl group or an ethylenically unsaturated group having 1 or more and 6 or less carbon atoms; m is an integer of 0 or more and 500 or less; in a case where m is 2 or more, $X_3$ and $X_4$ are same or different for each repeating unit; $Y_1$ and $Y_2$ are independently a linear hydrocarbon group or a branched hydrocarbon group having 1 or more and 20 or less carbon atoms having an ether bond or having no ether bond; $Z_1$ to $Z_4$ are independently hydrogen atom or an ethylenically unsaturated group; and at least one of $X_1$ to $X_6$ or $Z_1$ to $Z_4$ is an ethylenically unsaturated group.

4 Claims, No Drawings

DENTAL ADHESIVE COMPOSITION

TECHNICAL FIELD

The disclosures herein generally relate to a dental adhesive composition.

BACKGROUND ART

In the field of dentistry, with the spread of dental restorative materials such as composite resins, dental adhesive compositions that provide an adhesive effect between a tooth and the dental restorative materials have been used. For example, a dental adhesive composition including a polymerizable monomer having a phosphate group has been disclosed (see, for example, Patent Document 1).

In addition, dental compositions are used that form a uniform coating surface on a tooth (enamel and dentin) that is an adherend. For example, a dental composition including a copolymer having a monomer unit with a perfluoroalkyl group at least at a non-terminal position, or a copolymer having a monomer unit with a siloxy group at least at a non-terminal position, is disclosed (see, for example, Patent Document 2).

CITATION LIST

Patent Document

Patent Document 1: WO 2019/203356

Patent Document 2: Japanese Unexamined Patent Application Publication No. 2020-2076

SUMMARY OF INVENTION

Technical Problem

However, in the conventional dental adhesive composition, adhesive strength between the tooth and ceramics is not sufficient.

An object of the present invention is to provide a dental adhesive composition excellent in the adhesive strength between the tooth and the ceramics.

Solution to Problem

According to one aspect of the present disclosure, a dental adhesive composition includes: a (meth)acrylate having an acid group; and a linear siloxane represented by a general formula (1).

[Chem. 1]

(1)

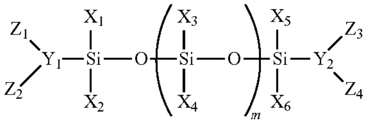

In the general formula (1), $X_1$ to $X_6$ are independently an alkyl group or an ethylenically unsaturated group having 1 or more and 6 or less carbon atoms; m is an integer of 0 or more and 500 or less; in a case where m is 2 or more, $X_3$ and $X_4$ are same or different for each repeating unit; $Y_1$ and $Y_2$ are independently a linear hydrocarbon group or a branched hydrocarbon group having 1 or more and 20 or less carbon atoms having an ether bond or having no ether bond; $Z_1$ to $Z_4$ are independently hydrogen atom or an ethylenically unsaturated group; and at least one of $X_1$ to $X_6$ or $Z_1$ to $Z_4$ is an ethylenically unsaturated group.

Advantageous Effects of Invention

According to one aspect of the present disclosure, a dental adhesive composition excellent in the adhesive strength between the tooth and the ceramics, can be provided.

DESCRIPTION OF EMBODIMENTS

In the following, embodiments of the present invention will be described in detail.

A dental adhesive composition according to the present embodiment contains a (meth)acrylate having an acid group, and a linear siloxane having a predetermined structure.

As used herein, a (meth)acrylate refers to a monomer, oligomer, or prepolymer having one or more (meth)acryloyloxy groups of (meth)acrylates. A (meth)acrylate refers to one or both of an acrylate and a methacrylate.

The siloxane is a structure represented by -silicon (Si)-oxygen (O)-[-silicon (Si)-oxygen (O)-]L-silicon (Si)— (L is an integer of 0 or more).

The (meth)acrylate having an acid group included in the dental adhesive composition is preferably, but not particularly limited to, a (meth)acrylate having an acid group of, for example, a phosphate group, a pyrophosphate group, a thiophosphate group, a carboxylic acid group, a sulfonic acid group, a phosphonic acid group, and the like. The (meth)acrylate having an acid group may include a plurality of acid groups.

Examples of the (meth)acrylate having a phosphate group include 2-(meth)acryloyloxyethyl dihydrogenphosphate, bis[2-(meth)acryloyloxyethyl]hydrogenphosphate, 2-(meth)acryloyloxyethyl phenyl hydrogenphosphate, 6-(meth)acryloyloxyhexyl dihydrogenphosphate, 6-(meth)acryloyloxyhexyl phenyl hydrogenphosphate, 10-(meth)acryloyloxydecyl dihydrogenphosphate, 1,3-di(meth)acryloyloylpropane-2 dihydrogenphosphate, 1,3-di(meth)acryloyloylpropane-2 phenyl hydrogenphosphate, bis[5-{2-(meth)acryloyloxyethoxycarbonyl} heptyl] hydrogenphosphate, and the like.

Examples of the (meth)acrylate having a pyrophosphate group include bis[2-(meth)acryloyloxyethyl] pyrophosphate, bis[4-(meth)acryloyloxybutyl] pyrophosphate, bis[6-(meth)acryloyloxyhexyl] pyrophosphate, bis[8-(meth)acryloyloxyoctyl] pyrophosphate, bis[10-(meth)acryloyloxydecyl] pyrophosphate, and the like.

Examples of the (meth)acrylate having a thiophosphate group include 2-(meth)acryloyloxyethyl dihydrogenthiophosphate, 3-(meth)acryloyloxypropyl dihydrogenthiophosphate, 4-(meth)acryloyloxybutyl dihydrogenthiophosphate, 5-(meth)acryloyloxypentyl dihydrogenthiophosphate, 6-(meth)acryloyloxyhexyl dihydrogenthiophosphate, 7-(meth)acryloyloxyheptyl dihydrogenthiophosphate, 8-(meth)acryloyloxyoctyl dihydrogenthiophosphate, 9-(meth)acryloyloxynonyl dihydrogenthiophosphate, 10-(meth)acryloyloxydecyl dihydrogenthiophosphate, 11-(meth)acryloyloxyundecyl dihydrogenthiophosphate, 12-(meth)acryloyloxydodecyl dihydrogenthiophosphate, 13-(meth)acryloyloxytridecyl dihydrogenthiophosphate, 14-(meth)acryloyloxytetradecyl dihydrogenthiophosphate, 15-(meth)acryloyloxypentadecyl dihydrogenthiophosphate, 16-(meth)acryloyloxyhexadecyl dihydrogenthiophosphate, 17-(meth)acryloyloxyheptadecyl dihydrogenthiophosphate, 18-

(meth)acryloyloxyoctadecyl dihydrogenthiophosphate, 19-(meth)acryloyloxynonadecyl dihydrogenthiophosphate, 20-(meth)acryloyloxyicosyl dihydrogenthiophosphate, and the like.

Examples of the (meth)acrylate having a carboxylic acid group include 2-methacryloyloxyethyl succinic acid, 4-(meth)acryloyloxyethyl trimellitic acid, 4-(meth)acryloyloxyethyl trimellitic anhydride, 4-(meth)acryloyloxydecyl trimellitic acid, 4-(meth)acryloyloxydecyl trimellitic anhydride, 11-(meth)acryloyloxy-1,1-undecandicarboxylic acid, 1,4-di(meth)acryloyloxypyromellitic acid, 2-(meth)acryloyloxyethyl maleic acid, 2-(meth)acryloyloxyethyl phthalic acid, 2-(meth)acryloyloxyethyl hexahydrophthalic acid, and the like.

Examples of the (meth)acrylate having a sulfonic acid group include 2-(meth)acrylamide-2 methylpropanesulfonic acid, styrene sulfonic acid, 2-sulfoethyl (meth)acrylate, and the like.

Examples of the (meth)acrylate having a phosphonic acid group include 2-(meth)acryloyloxyethyl phenylphosphonate, 5-(meth)acryloyloxypentyl-3 phosphonopropionate, 6-(meth)acryloyloxyhexyl-3 phosphonopropionate, 10-(meth)acryloyloxydecyl-3 phosphonopropionate, 6-(meth) acryloyloxyhexyl-3 phosphonoacetate, 10-(meth)acryloyloxydecyl-3 phosphonoacetate, and the like.

The (meth)acrylate having an acid group may be used alone or in combination of two or more.

Among these, as the (meth)acrylate having an acid group, a (meth)acrylate having one or more groups selected from a phosphate group, a thiophosphate group, and a carboxylic acid group is preferable, in terms of solubility of the smear layer on the tooth surface and tooth demineralization of the dental adhesive composition, especially in terms of adhesiveness to enamel.

Further, among these, as the (meth)acrylate having an acid group, one or more (meth)acrylates selected from 10-methacryloyloxydecyl dihydrogenphosphate (MDP), 4-methacryloyloxyethyl trimellitic anhydride (4-META), and the like are preferable, in terms of improving adhesiveness of the dental adhesive composition.

The content of the (meth)acrylate having an acid group in the dental adhesive composition is preferably, but not particularly limited to, 0.1 mass % or more and 40 mass % or less, more preferably 1 mass % or more and 25 mass % or less, and further preferably 5 mass % or more and 25 mass % or less.

When the content of the (meth)acrylate having an acid group in the dental adhesive composition is 0.1 mass % or more, the demineralization power of the dental adhesive composition to the tooth is further improved, and when the content is 40 mass % or less, the curability of the dental adhesive composition is improved.

The siloxane having a predetermined structure included in the dental adhesive composition is a linear siloxane represented by a general formula (1) below.

[Chem. 2]

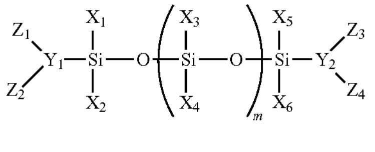

(1)

In the general formula (1), $X_1$ to $X_6$ are independently an alkyl group or an ethylenically unsaturated group having 1 or more and 6 or less carbon atoms. Here, independently means that the structures and carbon atoms of $X_1$ to $X_6$ may be different from each other.

The upper limit of the carbon atoms in $X_1$ to $X_6$ is not particularly limited, but is preferably 4, more preferably 3, and further preferably 2.

Examples of the alkyl group having 1 or more and 6 or less carbon atoms of $X_1$ to $X_6$ include, but not particularly limited to, a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a 3-methylpentyl group, a 2-methylpentyl group, a 2-ethylbutyl group, a 1,2-dimethylbutyl group, a 2,3-dimethylbutyl group, an n-heptyl group, and the like.

Examples of the ethylenically unsaturated group is not particularly limited, but include a vinyl group, an allyl group, an acrylic group (also referred to as an acryloyl group), a methacrylic group (also referred to as a methacryloyl group), and the like. The ethylenically unsaturated group may include an alkylene group having 1 or more and 6 or less carbon atoms.

In the general formula (1), m is an integer of 0 or more and 500 or less, preferably 0 or more and 300 or less, more preferably 0 or more and 100 or less, further preferably 0 or more and 50 or less, and particularly preferably 0 or more and 10 or less.

In a case where m is 2 or more, $X_3$ and $X_4$ may be the same or different for each repeating unit. Specifically, for example, when m is 2, one of the repeating units may be an alkyl group having 1 carbon atom in $X_3$ and $X_4$, and the other one of the repeating units may be an alkyl group having 2 carbon atoms in $X_3$ and $X_4$.

In the general formula (1), $Y_1$ and $Y_2$ are independently a linear hydrocarbon group or a branched hydrocarbon group having 1 or more and 20 or less carbon atoms. $Y_1$ and $Y_2$ may include an ether bond.

The term "a linear hydrocarbon group or a branched hydrocarbon group having 1 or more and 20 or less carbon atoms" refers to a linear hydrocarbon group having 1 or more and 20 or less carbon atoms or a branched hydrocarbon group having 1 or more and 20 or less carbon atoms.

The upper limit of the carbon atoms in $Y_1$ and $Y_2$ is preferably 16, more preferably 8, and further preferably 2.

Examples of the linear hydrocarbon group or the branched hydrocarbon group having 1 or more and 20 or less carbon atoms of $Y_1$ and $Y_2$ include, but not particularly limited to, structures represented by $C_\alpha H_{2\alpha}$ and $C_\alpha H_{2\alpha-1}$ ($\alpha$ is an integer of 1 or more and 20 or less).

In the general formula (1), $Z_1$ to $Z_4$ are independently hydrogen atom or an ethylenically unsaturated group. For example, when one of $Z_1$ and $Z_2$ is hydrogen and the other is the ethylenically unsaturated group, the ethylenically unsaturated group is an end group of the linear siloxane represented by the general formula (1). When both $Z_1$ and $Z_2$ are hydrogen atoms, $Y_1$ is the end group of the linear siloxane represented by the general formula (1).

When one of $Z_3$ and $Z_4$ is hydrogen and the other is the ethylenically unsaturated group, the ethylenically unsaturated group is the end group of the linear siloxane represented by the general formula (1). When both $Z_3$ and $Z_4$ are hydrogen atoms, $Y_2$ is the end group of the linear siloxane represented by the general formula (1).

In the general formula (1), at least one of $X_1$ to $X_6$ or $Z_1$ to $Z_4$ is the ethylenically unsaturated group.

That is, the linear siloxane represented by the general formula (1) may include the ethylenically unsaturated group at one end of the siloxane, may include the ethylenically unsaturated groups at both ends of the siloxane, and may include the ethylenically unsaturated group at the side chain.

It is preferable when the linear siloxane represented by the general formula (1) includes the ethylenically unsaturated group at the side chain, because a surface modification effect is obtained, crosslinking density is improved, and hardness is increased. When the siloxane includes the ethylenically unsaturated group at one end or both ends, a surface modification effect is obtained, crosslinking density is improved, and hardness is increased.

Specific Examples of the linear siloxane having at least one ethylenically unsaturated group include a linear siloxane having (meth)acryloyl groups at both ends of the siloxane, a linear siloxane having a (meth)acryloyloxy group at one end of the siloxane, and a linear siloxane having a (meth) acryloyloxy group at the side chain of the siloxane.

Examples of the linear siloxane having (meth)acryloyl groups at both ends include "X-22-164", "X-22-164AS", "X-22-164 A", "X-22-164B", "X-22-164C", "X-22-164E", "KP-410", "KP-411", "KP-412", "KP-413", "KP-414", "KP-415", "KP-423" (manufactured by Shin-Etsu Chemical Co., Ltd.), "DMS-C21", "DMS-E21", "DMS-T21", and "DMS-U21" (manufactured by Gelest, Inc.).

Examples of the linear siloxane having a (meth)acryloyloxy group at one end include "X-22-174ASX", "X-22-174BX", "KF-2012", "X-22-2426", "X-22-2404", "KP-416", "KP-418", "KP-422" (manufactured by Shin-Etsu Chemical Co., Ltd.), and the like.

Examples of the linear siloxane having a (meth)acryloyloxy group at the side chain include "KP-420" (manufactured by Shin-Etsu Chemical Co., Ltd.) and the like.

The linear siloxane may be used alone, or in combination of two or more.

The content of the linear siloxane in the dental adhesive composition is not particularly limited, but is preferably 0.01 mass % or more and 30 mass % or less, more preferably 0.1 mass % or more and 25 mass % or less, and further preferably 0.5 mass % or more and 20 mass % or less.

When the content of the linear siloxane in the dental adhesive composition is 0.01 mass % or more, the adhesive strength to the ceramics is improved by lowering the surface tension, and when the content is 30 mass % or less, the hydrophilicity of the dental adhesive composition is maintained and the adhesiveness to the tooth is improved.

The dental adhesive composition of the present embodiment may contain a (meth)acrylate having no acid group.

The (meth)acrylate having no acid group is not particularly limited. Example of the (meth)acrylate having no acid group include methyl (meth)acrylate, ethyl (meth)acrylate, isopropyl (meth)acrylate, n-butyl (meth)acrylate, isobutyl (meth)acrylate, hydroxypropyl (meth)acrylate, tetrahydrofurfuryl (meth)acrylate, glycidyl (meth)acrylate, 2-hydroxyethyl (meth)acrylate, 2-hydroxypropyl (meth)acrylate, 3-hydroxypropyl (meth)acrylate, 2-methoxyethyl (meth) acrylate, 2-ethoxyethyl (meth)acrylate, 2-methylhexyl (meth)acrylate, 2-ethylhexyl (meth)acrylate, benzyl (meth) acrylate, 2-hydroxy-1,3-di(meth)acryloyloxypropane, ethylene glycol di(meth)acrylate, diethylene glycol di(meth)acrylate, triethylene glycol di(meth)acrylate, butylene glycol di(meth)acrylate, neopentyl glycol di(meth)acrylate, 1,3-butanediol di(meth)acrylate, 1,4-butanediol di(meth)acrylate, 1,6-hexanediol di(meth)acrylate, trimethylolpropane tri (meth)acrylate, trimethylolethane tri(meth)acrylate, pentaerythritol tri(meth)acrylate, trimethylolmethane tri (meth)acrylate, pentaerythritol tetra (meth)acrylate, polybutylene glycol di(meth)acrylate, bisphenol A diglycidyl (meth)acrylate, di-2-(meth)acryloyloxyethyl-2,2,4-trimethylhexamethylenedicarbamate, 1,3,5-tris[1,3-bis {(meth) acryloyloxy}-2 propoxycarbonylaminohexane]-1,3,5-(1H, 3H,5H) triazine-2,4,6-trione, and 2,2-bis[4-(3-(meth) acryloyloxy-2 hydroxypropyl) phenyl]propane, N,N'-(2,2,4-trimethylhexamethylene) bis[2-(aminocarboxy) propane-1, 3-diol] tetramethacrylate, and the like.

The (meth)acrylate having no acid group may be used alone, or in combination of two or more.

Among these, as the (meth)acrylates having no acid group, 2-hydroxy-1,3-dimethacryloyloxypropane (GDMA), triethylene glycol dimethacrylate (TEGDMA), and bisphenol A diglycidyl methacrylate are preferable, in terms of improving the mechanical strength of the cured body of the dental adhesive composition and improving the adhesiveness to the ceramics and to the tooth.

The content of the (meth)acrylates having no acid group in the dental adhesive composition may be 3 mass % or more and 50 mass % or less, preferably 5 mass % or more and 40 mass % or less, and more preferably 10 mass % or more and 30 mass % or less.

When the content of the (meth)acrylate having no acid group in the dental adhesive composition is 3 mass % or more, the operability of the dental adhesive composition can be improved. When the content of the (meth)acrylate having no acid group in the dental adhesive composition is 50 mass % or less, the mechanical strength of the dental polymerizable composition can be improved.

The dental adhesive composition of the present embodiment may contain other components as long as they do not detract from the purpose of the present invention. Examples of the other components contained in the dental adhesive composition include a polymerization initiator, a polymerization inhibitor, a filler, and a solvent. Examples of the polymerization initiator include a chemical polymerization initiator and a photopolymerization initiator.

The chemical polymerization initiator is not particularly limited, but is, for example, a thiourea derivative, a vanadium compound, a tertiary amine, and an organic peroxide may be used.

Among the chemical polymerization initiator, the thiourea derivative functions as a reducing agent.

Examples of the thiourea derivative include, but not particularly limited to, ethylenethiourea, N-methylthiourea, N-ethylthiourea, N-propylthiourea, N-butylthiourea, N-laurylthiourea, N-phenylthiourea, N-cyclohexylthiourea, N,N-dimethylthiourea, N,N-diethylthiourea, N,N-dipropylthiourea, N,N-dibutylthiourea, N,N-dilaurylthiourea, N,N-diphenylthiourea, N,N-dicyclohexylthiourea, trimethylthiourea, tetramethylthiourea, N-acetylthiourea, N-benzoylthiourea, 1-allyl-3-(2-hydroxyethyl)-2 thiourea, 1-(2-tetrahydrofurfuryl)-2 thiourea, N-tert-butyl-N'-isopropylthiourea, 2-pyridylthiourea, and the like.

The thiourea derivative may be used alone, or in combination of two or more. Among these, N-benzoylthiourea is preferable in terms of improving the curability of the dental adhesive composition.

The content of the thiourea derivative in the dental adhesive composition is not particularly limited, but is preferably 0.1 mass % or more and 5 mass % or less, more preferably 0.1 mass % or more and 3 mass % or less, further preferably 0.1 mass % or more and 1 mass % or less. When the content of the thiourea derivative in the dental adhesive composition is 0.1 mass % or more, the curability of the dental adhesive composition is further improved, and when the content is 5 mass % or less, the solubility of the thiourea derivative in the (meth)acrylate in the dental adhesive composition is improved.

Among the chemical polymerization initiator, the vanadium compound functions as a reducing agent.

Examples of the vanadium compound include, but not particularly limited to, oxovanadium oxalate, vanadyl acetylacetonate, vanadium acetylacetonate, vanadyl stearate, vanadium naphthenate, vanadium benzoylacetonate, and the like.

The vanadium compound may be used alone, or in combination of two or more. Among these, vanadyl acetylacetonate is preferable in terms of the curability of the dental adhesive composition.

The content of the vanadium compound in the dental adhesive composition is not particularly limited, but is preferably 0.001 mass % or more and 5 mass % or less, more preferably 0.0015 mass % or more and 1 mass % or less, and further preferably 0.002 mass % or more and 0.1 mass % or less. When the content of the vanadium compound in the dental adhesive composition is 0.001 mass % or more, the curability of the dental adhesive composition is further improved, and when the content is 5 mass % or less the storage stability of the dental adhesive composition is further improved.

Among the chemical polymerization initiator, the tertiary amine functions as a reducing agent. The tertiary amine can also function as a photopolymerization accelerator.

Examples of the tertiary amine include, but not particularly limited to, a tertiary aliphatic amine and a tertiary aromatic amine.

Examples of the tertiary aliphatic amine include N,N-dimethylaminoethyl methacrylate, triethanolamine, and the like.

Examples of the tertiary aromatic amine include alkyl p-dialkylaminobenzoate, 7-dimethylamino-4 methylcoumarin, N,N-dimethylaniline, N,N-dibenzylaniline, N,N-dimethyl-p-toluidine, N,N-diethyl-p-toluidine, N,N-bis(2-hydroxyethyl)-p-toluidine, N,N,2,4,6-pentamethylaniline, N,N,2,4-tetramethylaniline, N,N-diethyl-2,4,6-trimethylaniline, and the like.

Among these, the tertiary amine is preferably the tertiary aromatic amine, and more preferably an alkyl p-dialkylaminobenzoate.

Examples of the alkyl p-dialkylaminobenzoate include methyl p-dimethylaminobenzoate, ethyl p-dimethylaminobenzoate (ethyl 4-dimethylaminobenzoate) (EPA), propyl p-dimethylaminobenzoate, amyl p-dimethylaminobenzoate, isoamyl p-dimethylaminobenzoate, ethyl p-diethylaminobenzoate, propyl p-diethylaminobenzoate, and the like.

The tertiary amine may be used alone, or in combination of two or more. Among them, ethyl 4-dimethylaminobenzoate (EPA) is preferable in terms of improving the curability of the dental adhesive composition.

The content of the tertiary amine in the dental adhesive composition is not particularly limited, but is preferably 0.01 mass % or more and 10 mass % or less, more preferably 0.05 mass % or more and 8 mass % or less, and further preferably 1 mass % or more and 5 mass % or less. When the content of the tertiary amine in the dental adhesive composition is 0.01 mass % or more, the curability of the dental adhesive composition is further improved, and when the content is 10 mass % or less, the working time with the dental adhesive composition is increased, thereby ensuring sufficient working time.

Among the chemical polymerization initiator, the organic peroxide functions as an oxidizing agent.

Examples of the organic peroxide include benzoyl peroxide, cumene hydroperoxide, t-butyl hydroperoxide, t-amyl hydroperoxide, 1,1,3,3-tetramethylbutyl hydroperoxide, 2,5-dimethyl-2,5-di(hydroperoxy) hexane, p-diisopropylbenzene monohydroperoxide, p-methane hydroperoxide, pinane hydroperoxide, and the like.

The organic peroxide may be used alone, or in combination of two or more. Among these, cumene hydroperoxide is preferable in terms of the curability of the dental adhesive composition.

The content of the organic peroxide in the dental adhesive composition is not particularly limited, but is preferably 0.01 mass % or more and 10 mass % or less, more preferably 0.05 mass % or more and 5 mass % or less, further preferably 0.1 mass % or more and 3 mass % or less. When the content of the organic peroxide in the dental adhesive composition is 0.01 mass % or more, the curability of the dental adhesive composition is further improved, and when the content is 10 mass % or less, the working time with the dental adhesive composition is increased, thereby ensuring sufficient working time.

Examples of the photopolymerization initiator include, but not particularly limited to, camphorquinone (CQ), 2,4,6-trimethylbenzoyldiphenylphosphine oxide (TPO), phenylbis(2,4,6-trimethylbenzoyl) phosphine oxide, benzyl ketal, diacetyl ketal, benzyl dimethyl ketal, benzyl diethyl ketal, benzyl bis(2-methoxyethyl) ketal, 4,4'-dimethyl (benzyl dimethyl ketal), anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diethylthioxanthone, 2,4-diisopropylthioxanthone, 2-chloro-7 trifluoromethylthioxanthone, thioxanthone-10,10 dioxide, thioxanthone-10-oxide, benzoin methyl ether, benzoin ethyl ether, benzoin isopropyl ether, benzoin isobutyl ether, benzophenone, bis(4-dimethylaminophenyl) ketone, 4,4'-bis(diethylamino) benzophenone, and the like.

The photopolymerization initiator may be used alone, or in combination of two or more. Among them, camphorquinone (CQ) and 2,4,6-trimethylbenzoyldiphenylphosphine oxide (TPO) are preferable in terms of improving the curability of the dental adhesive composition.

The content of the photopolymerization initiator in the dental adhesive composition is not particularly limited, but is preferably 0.01 mass % or more and 10 mass % or less, more preferably 0.05 mass % or more and 8 mass % or less, and further preferably 1 mass % or more and 5 mass % or less. When the content of the photopolymerization initiator in the dental adhesive composition is 0.01 mass % or more, the curability of the dental adhesive composition is further improved, and when the content is 10 mass % or less, the working time with the dental adhesive composition is increased, thereby ensuring sufficient working time.

Because the dental adhesive composition of the present embodiment is often cured by irradiation with ultraviolet rays or the like, it is preferable that the photopolymerization initiator is included as the polymerization initiator.

Examples of the polymerization inhibitor include dibutylhydroxytoluene (2,6-di-tert-butyl-p-cresol) (BHT), 6-tert-butyl-2,4-xylenol, and the like.

The polymerization inhibitor may be used alone, or in combination of two or more. Among them, dibutylhydroxytoluene (BHT) is preferable in terms of improving the curability of the dental adhesive composition.

The content of the polymerization inhibitor in the dental adhesive composition is not particularly limited, but is preferably 0.01 mass % or more and 5 mass % or less, more preferably 0.05 mass % or more and 3 mass % or less, and further preferably 0.1 mass % or more and 1 mass % or less. When the content of the polymerization inhibitor in the dental adhesive composition is 0.01 mass % or more and 5 mass % or less, the storage stability of the dental adhesive composition is improved.

Examples of the filler include, but not particularly limited to, colloidal silica; fine particle silica in which the surface is hydrophobized (hydrophobic fumed silica); aluminum oxide; fluoroaluminosilicate glass; barium glass; and the like. Among these, hydrophobic fumed silica (for example, Aerosil (registered trademark)) is preferable. The filler may be used alone, or in combination of two or more.

The content of the filler in the dental adhesive composition is preferably, for example, 0.1 mass % or more and 30 mass % or less, more preferably 0.5 mass % or more and 20 mass % or less, further preferably 1 mass % or more and 10 mass % or less.

When the content of the filler in the dental adhesive composition is 0.1 mass % or more, the viscosity of the dental adhesive composition increases, and the operability of the dental adhesive composition can be improved. When the content of the filler in the dental adhesive composition is 30 mass % or less, the viscosity of the dental adhesive composition containing the glass does not become too high, and the high operability of the dental adhesive composition can be maintained.

Examples of the solvent include, but not particularly limited to, one or more solvent selected from water and an organic solvent.

Examples of the water include, but not particularly limited to, ion exchanged water or distilled water. When the dental adhesive composition contains water, the acid group of the (meth)acrylate having the acid group is dissociated. Therefore, the solubility of the smear layer on the tooth surface; and the tooth demineralization and the permeability to the tooth, which are functions as a primer of the dental adhesive composition, are improved, and the adhesiveness of the dental adhesive composition is improved.

The content of water in the dental adhesive composition is not particularly limited, but is, for example, preferably 1 mass % or more and 50 mass % or less, more preferably 5 mass % or more and 40 mass % or less, and more preferably 10 mass % or more and 30 mass % or less. When the content of water in the dental adhesive composition is 1 mass % or more and 50 mass % or less, the solubility of the smear layer on the tooth surface; and the tooth demineralization and the permeability to the tooth, which are functions as a primer of the dental adhesive composition, are improved.

Examples of the organic solvent include ethanol, acetone, 1-propanol, 2-propanol, ethyl methyl ketone, and the like.

The content of the organic solvent in the dental adhesive composition is not particularly limited, but is preferably 5 mass % or more and 60 mass % or less, more preferably 10 mass % or more and 50 mass % or less, and further preferably 20 mass % or more and 40 mass % or less. When the content of the organic solvent in the dental adhesive composition is 5 mass % or more, the uniformity of the dental adhesive composition is improved, and when the content is 60 mass % or less, the adhesiveness of the dental adhesive composition is improved.

In the dental adhesive composition of the present embodiment, by containing the (meth)acrylate having an acid group and the linear siloxane represented by the general formula (1) as described above, it is possible to exhibit an excellent adhesive strength not only to the tooth but also to the ceramics.

Specifically, the dental adhesive composition of the present embodiment can exhibit a high adhesiveness to any of the ceramics, enamel, and dentin. Therefore, the dental adhesive composition of the present embodiment can enhance the adhesiveness between ceramic dental artifacts (for example, dental prosthetics) and a tooth.

Further, in the dental adhesive composition of the present embodiment, by containing the (meth)acrylate having no acid group as described above, the mechanical strength of the cured body of the dental adhesive composition can be improved, and the adhesiveness to the ceramics and to the tooth can be further improved.

The application of the dental adhesive composition of the present embodiment is not particularly limited, but it can be used for various dental materials, for example.

Examples of the dental materials include dental cement, dental adhesive, dental temporary sealing material, dental primer, dental coat material, dental composite resin, dental hard resin, dental cutting resin material, dental temporary restorative material, dental filler, and dentifrice. Among them, the dental adhesive composition according to the present embodiment is suitably used for dental adhesive, dental composite resin, and dental cement.

EXAMPLES

Hereinafter, the present invention will be further described with reference to Examples. In the following, numerical values without units, "parts" or "%" are based on mass unless otherwise specified.

<Preparation of Bonding Material>

Bonding materials (Examples 1 to 12 and Comparative Examples 1 to 3) with the composition presented in Table 1 were prepared. Each of the bonding materials was prepared by mixing methacrylates having an acid group, a silicone compound, methacrylates having no acid group, polymerization initiators, a polymerization inhibitor, a filler, an organic solvent, and water.

<Adhesive Strength to Ceramic>

A ceramic was polished with #600 water-resistant abrasive paper, and hydrofluoric acid was applied to the flat polished surface. After standing for 10 seconds, the surface was washed off with distilled water, and ultrasonic cleaning for 10 minutes was performed twice. The prepared bonding material was applied to the surface, and the surface was immediately dried by air blowing.

Next, a plastic mold with a hole of 2.38 mm in diameter was placed on the test surface, and the mold was irradiated with light using a light irradiator (G-Light Prima II Plus, manufactured by GC Corporation) for 10 seconds, filled with composite resin, and irradiated with light for another 20 seconds. The plastic mold was immersed in water at 37° C. for 24 hours, and then thermally cycled between 5° C. and 55° C. for 5000 cycles.

Using an autograph (small tabletop tester EZ-S manufactured by Shimadzu Corporation), five prepared specimens were subjected to shear tests at a crosshead speed of 1 mm/min, and the average value of the shear bond strength was obtained to evaluate the adhesiveness of the composite resin to the ceramic when the bonding material was used.

The evaluation criteria for the adhesiveness of the composite resin to the ceramic (the adhesive strength to the ceramic) when the bonding materials are used are as follows. When the evaluation is A or B, it is determined as good, and when the evaluation is C, it is determined as poor.

[Evaluation Criteria]

A: the average of the shear bond strength is 20 MPa or more

B: the average of the shear bond strength is 15 MPa or more and less than 20 MPa C: the average of the shear bond strength is less than 15 MPa <Adhesive Strength to Enamel and Adhesive Strength to Dentin>

A tooth was polished with #400 water-resistant abrasive paper to expose the fresh surface. The bonding material was applied and immediately dried by air blowing.

A plastic mold with a hole of 2.38 mm in diameter was placed on the test surface, and the mold was irradiated with light using a light irradiator (G-Light Prima II Plus, manufactured by GC Corporation) for 10 seconds, filled with composite resin, and irradiated with light for another 20 seconds. The plastic mold was immersed in water at 37° C. for 24 hours. Using the autograph (small tabletop tester EZ-S manufactured by Shimadzu Corporation), five specimens were subjected to shear tests at a crosshead speed of 1 mm/min, and the average value of the shear bond strength was obtained to evaluate the adhesiveness of the composite resin to the dentin when the bonding material was used.

The evaluation criteria for the adhesiveness of the composite resin to the dentin (enamel and dentin) when the bonding materials are used are as follows. When the evaluation is A or B, it is determined as good, and when the evaluation is C, it is determined as poor.

[Evaluation Criteria]

A: the average of the shear bond strength is 25 MPa or more

B: the average of the shear bond strength is 15 MPa or more and less than 25 MPa C: the average of the shear bond strength is less than 15 MPa Examples and Comparative Examples will be described below.

Example 1

5 parts of 4-methacryloyloxyethyl trimellitic anhydride (4-META) and 5 parts of 10-methacryloyloxydecyl dihydrogenphosphate (MDP) as the methacrylates having an acid group; 1.2 parts of linear siloxane having (meth)acryloyl groups at both ends (manufactured by Shin-Etsu Chemical Co., Ltd., KP-410) as the silicone compounds; 15 parts of 2-hydroxy-1,3-dimethacryloyloxypropane (GDMA) and 5 parts of triethyleneglycol dimethacrylate (TEGDMA) as the methacrylates having no acid group; 2 parts of 2,4,6-trimethylbenzoyldiphenylphosphine oxide (TPO), 1.0 parts of camphorquinone (CQ), and 1 part of ethyl 4-dimethylaminobenzoate (EPA), as the polymerization initiator; 1 part of dibutylhydroxytoluene (2,6-di-tert-butyl-p-cresol) (BHT) as the polymerization inhibitor; 5 parts of hydrophobic fumed silica (Aerosil (registered trademark) R972, manufactured by Nippon Aerosil Co., Ltd.) as the filler; 33.8 parts of acetone as the organic solvent; and 25 parts of water (distilled water) were blended. The results are presented in Table 1.

Example 2

A mixture was prepared in the same manner as in Example 1, except that 6 parts of 4-META, 12 parts of MDP, 5.0 parts of KP-410, 12 parts of GDMA, 1.2 parts of CQ, 29.8 parts of acetone, and 20 parts of distilled water were blended. The results are presented in Table 1.

Example 3

A mixture was prepared in the same manner as in Example 1, except that 9 parts of 4-META, 7 parts of MDP, 9.9 parts of KP-410, 10 parts of GDMA, 1.8 parts of CQ, 30.3 parts of acetone, and 18 parts of distilled water were blended. The results are presented in Table 1.

Example 4

A mixture was prepared in the same manner as in Example 1, except that 2.3 parts of linear siloxane having a (meth)acryloyl group at one end (KP-422, manufactured by Shin-Etsu Chemical Co., Ltd.) were blended in place of KP-410, and that 13 parts of 4-META, 9 parts of MDP, 0.8 parts of CQ, 24.9 parts of acetone, and 21 parts of distilled water were blended. The results are presented in Table 1.

Example 5

A mixture was prepared in the same manner as in Example 4, except that 6 parts of 4-META, 14 parts of MDP, 6.1 parts of KP-422, 12 parts of GDMA, 1.9 parts of CQ, 31.0 parts of acetone, and 15 parts of distilled water were blended. The results are presented in Table 1.

Example 6

A mixture was prepared in the same manner as in Example 4, except that 11 parts of 4-META, 11 parts of MDP, 12.1 parts of KP-422, 10 parts of GDMA, 2.3 parts of CQ, 24.6 parts of acetone, and 15 parts of distilled water were blended. The results are presented in Table 1.

Example 7

A mixture was prepared in the same manner as in Example 1, except that 0.5 parts of linear siloxane having (meth)acryloyl groups at both ends (KP-423, manufactured by Shin-Etsu Chemical Co., Ltd.) were blended in place of KP-410, and that 12 parts of 4-META, 6 parts of MDP, 1.1 parts of CQ, 30.4 parts of acetone, and 21 parts of distilled water were blended. The results are presented in Table 1.

Example 8

A mixture was prepared in the same manner as in Example 7, except that 13 parts of 4-META, 7 parts of MDP, 4.3 parts of KP-423, 12 parts of GDMA, 1.0 parts of CQ, and 27.7 parts of acetone were blended. The results are presented in Table 1.

Example 9

A mixture was prepared in the same manner as in Example 7, except that 7 parts of 4-META, 12 parts of MDP, 14.8 parts of KP-423, 10 parts of GDMA 1.4 parts of CQ, 25.8 parts of acetone, and 15 parts of distilled water were blended. The results are presented in Table 1.

Example 10

A mixture was prepared in the same manner as in Example 1, except that 1.8 parts of linear siloxane having (meth)acryloyl groups at both ends (DMS-U21, manufactured by Gelest, Inc.) were blended in place of KP-410, that 8 parts of 4-META, 4 parts of MDP, 2.0 parts of CQ, 27.2 parts of acetone, and 28 parts of distilled water were blended. The results are presented in Table 2.

Example 11

A mixture was prepared in the same manner as in Example 10, except that 5 parts of 4-META, 10 parts of MDP, 3.9 parts of DMS-U21, 12 parts of GDMA, 1.0 parts of CQ, 35.1 parts of acetone, and 19 parts of distilled water were blended. The results are presented in Table 2.

Example 12

A mixture was prepared in the same manner as in Example 10, except that 10 parts of 4-META, 8 parts of MDP, 7.5 parts of DMS-U21, 10 parts of GDMA, 2.5 parts of CQ, 32.0 parts of acetone, and 16 parts of distilled water were blended. The results are presented in Table 2.

Comparative Example 1

The preparation was performed in the same manner as in Example 1, except that no silicone compound was added (0 parts), and that 15 parts of 4-META, 8 parts of MDP, 2.3 parts of CQ, 25.7 parts of acetone, and 20 parts of distilled water were blended. The results are presented in Table 2.

Comparative Example 2

A mixture was prepared in the same manner as in Example 1, except that 3.6 parts of dimethylsilicone (a siloxane without (meth)acryloyl group) (KF-96L-2cs, manufactured by Shin-Etsu Chemical Co., Ltd.) were blended in place of KP-410, and that 8 parts of 4-META, 6 parts of MDP, 12 parts of GDMA, 2.2 parts of CQ, 39.2 parts of acetone, and 15 parts of distilled water were blended. The results are presented in Table 2.

Comparative Example 3

A mixture was prepared in the same manner as in Example 1, except that 11.4 parts of siloxane-containing acrylic polymer (KL-700, manufactured by Kyoeisha Chemical Co., Ltd.) were blended in place of KP-410, and that 7 parts of 4-META, 9 parts of MDP, 10 parts of GDMA, 1.6 parts of CQ, 24.0 parts of acetone, and 23 parts of distilled water were blended. The results are presented in Table 2.

TABLE 1

| | | EXAMPLE | | | | | | | | |
|---|---|---|---|---|---|---|---|---|---|---|
| | | 1 | 2 | 3 | 4 | 5 | 6 | 7 | 8 | 9 |
| ORGANIC SOLVENT | ACETONE | 33.8 | 29.8 | 30.3 | 24.9 | 31.0 | 24.6 | 30.4 | 27.7 | 25.8 |
| WATER | DISTILLED WATER | 25 | 20 | 18 | 21 | 15 | 15 | 21 | 21 | 15 |
| POLYMERIZATION INITIATOR | TPO | 2 | 2 | 2 | 2 | 2 | 2 | 2 | 2 | 2 |
| | CQ | 1.0 | 1.2 | 1.8 | 0.8 | 1.9 | 2.3 | 1.1 | 1.0 | 1.4 |
| | EPA | 1 | 1 | 1 | 1 | 1 | 1 | 1 | 1 | 1 |
| POLYMERIZATION INHIBITOR | BHT | 1 | 1 | 1 | 1 | 1 | 1 | 1 | 1 | 1 |
| METHACRYLATE HAVING ACID GROUP | 4-META | 5 | 6 | 9 | 13 | 6 | 11 | 12 | 13 | 7 |
| | MDP | 5 | 12 | 7 | 9 | 14 | 11 | 6 | 7 | 12 |
| METHACRYLATE HAVING NO ACID GROUP | GDMA | 15 | 12 | 10 | 15 | 12 | 10 | 15 | 12 | 10 |
| | TEGDMA | 5 | 5 | 5 | 5 | 5 | 5 | 5 | 5 | 5 |
| SILICONE COMPOUND | KP-410 | 1.2 | 5.0 | 9.9 | | | | | | |
| | KP-422 | | | | 2.3 | 6.1 | 12.1 | | | |
| | KP-423 | | | | | | | 0.5 | 4.3 | 14.8 |
| | DMS-U21 | | | | | | | | | |
| | KF-96L-2cs | | | | | | | | | |
| | KL-700 | | | | | | | | | |
| FILLER | R972 | 5 | 5 | 5 | 5 | 5 | 5 | 5 | 5 | 5 |
| TOTAL | | 100 | 100 | 100 | 100 | 100 | 100 | 100 | 100 | 100 |
| ADHESIVE STRENGTH TO CERAMICS [MPa] | | B 18.9 | A 21.8 | B 19.6 | B 17.9 | A 22.8 | B 19.5 | A 20.8 | B 16.4 | B 17.4 |
| ADHESIVE STRENGTH TO ENAMEL [MPa] | | A 30.2 | A 28.4 | A 29.2 | A 25.4 | A 25.8 | B 22.2 | A 27.5 | A 29.8 | A 25.5 |
| ADHESIVE STRENGTH TO DENTIN [MPa] | | A 27.1 | A 25.4 | A 30.7 | B 24.9 | B 22.8 | B 18.5 | A 28.7 | B 24.7 | A 27.2 |

TABLE 2

| | | EXAMPLE | | | COMPARATIVE EXAMPLE | | |
|---|---|---|---|---|---|---|---|
| | | 10 | 11 | 12 | 1 | 2 | 3 |
| ORGANIC SOLVENT | ACETONE | 27.2 | 35.1 | 32.0 | 25.7 | 39.2 | 24.0 |
| WATER | DISTILLED WATER | 28 | 19 | 16 | 20 | 15 | 23 |

TABLE 2-continued

| | | EXAMPLE | | | COMPARATIVE EXAMPLE | | |
|---|---|---|---|---|---|---|---|
| | | 10 | 11 | 12 | 1 | 2 | 3 |
| POLYMERIZATION INITIATOR | TPO | 2 | 2 | 2 | 2 | 2 | 2 |
| | CQ | 2.0 | 1.0 | 2.5 | 2.3 | 2.2 | 1.6 |
| | EPA | 1 | 1 | 1 | 1 | 1 | 1 |
| POLYMERIZATION INHIBITOR | BHT | 1 | 1 | 1 | 1 | 1 | 1 |
| METHACRYLATE HAVING ACID GROUP | 4-META | 8 | 5 | 10 | 15 | 8 | 7 |
| | MDP | 4 | 10 | 8 | 8 | 6 | 9 |
| METHACRYLATE HAVING NO ACID GROUP | GDMA | 15 | 12 | 10 | 15 | 12 | 10 |
| | TEGDMA | 5 | 5 | 5 | 5 | 5 | 5 |
| SILICONE COMPOUND | KP-410 | | | | | | |
| | KP-422 | | | | | | |
| | KP-423 | | | | | | |
| | DMS-U21 | 1.8 | 3.9 | 7.5 | | | |
| | KF-96L-2cs | | | | | 3.6 | |
| | KL-700 | | | | | | 11.4 |
| FILLER | R972 | 5 | 5 | 5 | 5 | 5 | 5 |
| TOTAL | | 100 | 100 | 100 | 100 | 100 | 100 |
| ADHESIVE STRENGTH TO CERAMICS [MPa] | | B 19.5 | A 21.1 | B 17.6 | C 12.9 | C 14.6 | C 11.9 |
| ADHESIVE STRENGTH TO ENAMEL [MPa] | | A 28.2 | A 28.8 | A 27.1 | A 27.9 | A 25.6 | C 11.7 |
| ADHESIVE STRENGTH TO DENTIN [MPa] | | A 27.6 | A 26.9 | A 25.1 | A 32.4 | B 22.9 | C 11.6 |

Table 1 indicates that bonding agents containing methacrylates having an acid group and a linear siloxane having a (meth)acryloyl group exhibit good adhesive strength to all ceramics, enamel, and dentin (Examples 1 to 12).

In contrast, bonding agents not containing a linear siloxane having a (meth)acryloyl group exhibit poor adhesive strength to at least one of ceramics, enamel, and dentin (Comparative Examples 1 to 3).

The embodiments disclosed above include, for example, the following aspects.

(Supplementary Note 1)

A dental adhesive composition including: a (meth)acrylate having an acid group; and a linear siloxane represented by a general formula (1).

[Chem. 3]

(1)

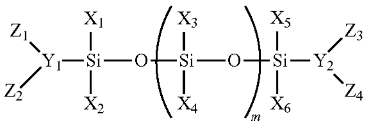

In the general formula (1), $X_1$ to $X_6$ are independently an alkyl group or an ethylenically unsaturated group having 1 or more and 6 or less carbon atoms; m is an integer of 0 or more and 500 or less; in a case where m is 2 or more, $X_3$ and $X_4$ are same or different for each repeating unit; $Y_1$ and $Y_2$ are independently a linear hydrocarbon group or a branched hydrocarbon group having 1 or more and 20 or less carbon atoms having an ether bond or having no ether bond; $Z_1$ to $Z_4$ are independently hydrogen atom or an ethylenically unsaturated group; and at least one of $X_1$ to $X_6$ or $Z_1$ to $Z_4$ is an ethylenically unsaturated group.

(Supplementary Note 2)

The dental adhesive composition of Supplementary Note 1, further including a (meth)acrylate having no acid group.

(Supplementary Note 3)

The dental adhesive composition of Supplementary Note 1 or 2, further including a photopolymerization initiator.

(Supplementary Note 4)

The dental adhesive composition of any one of Supplementary Notes 1 to 3, further including water.

While embodiments of the invention have been described, the invention is not limited to specific embodiments, and various modifications and variations are possible within the scope of the invention as claimed.

The present application is based on and claims priority to Japanese Patent Application No. 2021-162363, filed Sep. 30, 2021, and Japanese Patent Application No. 2022-141589, filed Sep. 6, 2022, the contents of which are incorporated herein by reference in their entirety.

The invention claimed is:

1. A dental adhesive composition comprising:

a (meth)acrylate having an acid group; and a linear siloxane represented by a general formula (1), (1)

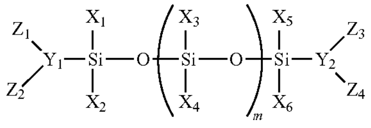

wherein in the general formula (1), $X_1$ to $X_6$ are independently an alkyl group or an ethylenically unsaturated group having 1 or more and 6 or less carbon atoms; m is an integer of 0 or more and 500 or less; in a case where m is 2 or more, $X_3$ and $X_4$ are same or different for each repeating unit; $Y_1$ and $Y_2$ are independently a linear hydrocarbon group or a branched hydrocarbon group having 1 or more and 20 or less carbon atoms having an ether bond or having no ether bond; $Z_1$ to $Z_4$ are independently hydrogen atom or an ethylenically unsaturated group; and at least one of $X_1$ to $X_6$ or $Z_1$ to $Z_4$ is an ethylenically unsaturated group.

2. The dental adhesive composition according to claim 1, further comprising a (meth)acrylate having no acid group.

3. The dental adhesive composition according to claim 1, further comprising a photopolymerization initiator.

4. The dental adhesive composition according to claim 1, further comprising water.

* * * * *